(12) United States Patent
Lazzeri et al.

(10) Patent No.: US 7,749,549 B2
(45) Date of Patent: Jul. 6, 2010

(54) USE OF SEED FLOUR AS SOIL PESTICIDE

(75) Inventors: Luca Lazzeri, Florence (IT); Onofrio Leoni, Castel San Pietro Terme (IT); Luisa M. Manici, Bologna (IT); Sandro Palmieri, Bologna (IT); Giampiero Patalano, Pisa (IT)

(73) Assignee: Cerealtoscana —S.p.A. (IT)

( * ) Notice: Subject to any disclaimer, the term of this patent is extended or adjusted under 35 U.S.C. 154(b) by 851 days.

(21) Appl. No.: 10/525,428

(22) PCT Filed: Aug. 22, 2003

(86) PCT No.: PCT/IT03/00514

§ 371 (c)(1),
(2), (4) Date: Dec. 9, 2005

(87) PCT Pub. No.: WO2004/017739

PCT Pub. Date: Mar. 4, 2004

(65) Prior Publication Data
US 2006/0111238 A1 May 25, 2006

(30) Foreign Application Priority Data
Aug. 23, 2002 (IT) .......................... BO2002A0544

(51) Int. Cl.
*A61K 36/31* (2006.01)
*A01N 25/00* (2006.01)
*A61K 36/00* (2006.01)

(52) U.S. Cl. .................................... 424/755; 504/116.1
(58) Field of Classification Search .................. 424/755; 504/116.1
See application file for complete search history.

(56) References Cited

U.S. PATENT DOCUMENTS 5,525,746 A * 6/1996 Franke .......................... 554/12
6,596,323 B1 7/2003 Deuel

FOREIGN PATENT DOCUMENTS

WO    WO-97 14309 A    4/1997

OTHER PUBLICATIONS

Brown, P. D.; Morra, M. J.; McCaffrey, J. P.; Auld, D. L.; Williams, L., III. Allelochemicals produced during glucosinolate degradation in soil. J. Chem. Ecol. 1991, 17, 2021-2034.*
Masayuki Taniguchi et al.,Agricultural and Biological Chemistry vol. 51, No. 2(1987)pp. 413-417.*
European Examination Report dated Feb. 13, 2007; Application No. 03 792 616.9-1219; Applicant Cereal Toscana S.P.A.
Sarwar et al., "Biofumigation potential of brassicas," Plant and Soil (1998) 201: 103-112.

Elberson, Leslie R et al: "Toxicity of rapeseed meal-amended soil to wireworms, *Limonius californicus* (Coleoptera: Elateridae)",Journal of Agricultural Entomology, vol. 13, No. 4, 1996, pp. 323-330, 1996. Abstract only.
Hafez, S.L. et al.: "Efficacy of oil seed meals for management of *Heterodera schachtii* and *Meloidogyne chitwoodi* under green house conditions" Phytopathology, vol. 91, No. 6, p. S135 Supplement, Jun. 2001, Joint Meeting of the American Phytopathological Society, and the Mycological Society of America; Salt Lake City, Utah, USA; Aug. 25-29, 2001. Abstract only.
Borek, Vladimir et al: "Toxicity of rapeseed meal and methyl isothiocyanate to larvae of the black vine weevil (Coleoptera: Curculionidae)" Journal of Economic Entomology, vol. 90, No. 1, 1997, pp. 109-112. Abstract only.
Siddiqui, M.A. et al: "Integrated control of plant parasitic nematodes with organic soil amendments/nematicides and ploughing on okra" Proceedings of the Indian National Science Academy Part B Biological, vol. 63, No. 6, pp. 545-550, Dec. 1997. Abstract only.
Wallingford, Oxon, GB; Anver, S. et al.: "Organic management of concomitant *Meloidogyne incognita* and *Rotylenchus reniformis* on chickpea" Allelopathy Journal, vol. 7, No. 1, pp. 79-84, 2000. Abstract only.
Oxon, GB; Anver, S. et al.: "Biological control of soil nematodes associated with linseed" Archives of Phytopathology and Plant Protection, vol. 34, No. 2, pp. 101-109, 2001. Abstract only.
Oxon, GB; Tiyagi, S.A. et al.: "Biodegradable effects of oilseed cakes on plant parasitic nematodes and soil-inhabiting fungi infesting *Trigonella foenum-graecum* and *Phaseolus aureus*" Indian Journal of Nematology, vol. 32, No. 1, pp. 47-57, 2002. Abstract only.
Tiyagi, Sartaj A et al: "Efficacy of oil-seed cakes against plant-parasitic nematodes and soil-inhabiting fungi on mungbean and chickpea" Bioresource Technology, vol. 51, No. 2-3, pp. 233-239, 1995. Abstract only.
Sarwar, M. et al: "Biofumigation potential of brassicas. III. In vitro toxicity of isothiocyanates to soil-borne fungal pathogens" Plant and Soil, vol. 201, No. 1, pp. 103-112, Apr. 1998. Abstract only.
Tsai, Rong et al; "Factors affecting the dissolution and degradation of oriental mustard-derived sinigrin and allyl isothicyanate in aqueous media" Journal of Agricultural and Food Chemistry, vol. 48, No. 5, pp. 1898-1902; May 2000. Abstract only.
Kumar, Krishan et al: "Efficacy of organic-amendments on the yield and control of *Aphelenchoides composticola* infesting mushroom, *Agaricus bisporus* (Lange) Sing" Indian Journal of Nematology, vol. 23, No. 1,pp. 82-86, 1993. Abstract only.
Jakhar, S.S. et al: "Effect of soil amendment with some oil cakes on root rot of cotton caused by *Rhizoctania* sp." Plant Disease Research, vol. 17, No. 1, pp. 16-20, 2002. Abstract only.
Mazzola, Mark et al: "Suppression of specific apple root pathogens by *Brassica napus* seed meal amendment regardless of glucosinolate content" Phytopathology, vol. 91, No. 7, pp. 673-679, Jul. 2001. Abstract only.
Brown, Paul D. et al: "Glucosinolate-containing plant tissues as bioherbicides" Journal of Agricultural and Food Chemistry vol. 43, No. 12, pp. 3070-3074;1995. Abstract only.
Manici, Luisa M. et al: "In vitro fungitoxic activity of some glucosinolates and their enzyme-derived products toward plant pathogenic fungi" Journal of Agricultural and Food Chemistry, vol. 45, No. 7, pp. 2768-2773; 1997. Abstract only.

(Continued)

*Primary Examiner*—Johann R Richter
*Assistant Examiner*—Courtney Brown
(74) *Attorney, Agent, or Firm*—Sheridan Ross P.C.

(57) ABSTRACT

Use of vegetable seed flour, in particular Brassicaceae flour, as a cytotoxic agent with improving action.

18 Claims, No Drawings

OTHER PUBLICATIONS

Palmieri, S.: "The Glucosinolate Myrosinase System—A Natural & Practical Tool for Biofumigation" Horticulture Biofumigation Update, No. 12, pp. 1-2, Nov. 2000.

Angelini, L. et al: "Antigerminative activity of three glucosinolate-derived products generated by myrosinase hydrolysis" Seed Science and Technology, vol. 26, No. 3, pp. 771-780, 1998. Abstract only.

Rodman, J.E.: "A Taxonomic Analysis of Glucosinolate-Producing Plants Part 2 Cladistics" Systematic Botany, vol. 16, No. 4, pp. 619-629, 1991. Abstract only.

Frohne, D. et al: "Systematik des Pflanzenreiches" 1998, Wissenschaftliche Verlagsgesellschaft MBH, Stuttgart, Ordungsgruppe Senfartige pp. 204-211; 1998.

International Search Report for PCT/IT03/00514.

* cited by examiner

USE OF SEED FLOUR AS SOIL PESTICIDE

TECHNICAL FIELD

The present invention concerns a use of seed flour as a soil improving agent, as a cytotoxic agent for soil pathogens and parasites, and as a fungitoxic agent for soil fungal pathogens.

BACKGROUND ART

In the agricultural sector methyl bromide is commonly used to limit the growth of fungal pathogens, nematodes, wireworms, insects, bacteria and weeds. However, methyl bromide has a relatively high environmental impact: reacting with the ozone present in the upper layer of the atmosphere, it transforms it into $Br_2O$, contributing to destruction of the ozone.

Recently, to replace methyl bromide, molecules of vegetable origin with cytotoxic activity for soil pathogens and parasites have been proposed. Among these molecules, derivatives of glucosinolates (GLs) generated by hydrolysis catalysed by the enzyme myrosinase (MYR) or by thermolysis have been proposed. The GLs are anionic thioglucosidic compounds present in variable quantities and ratios in a number of organisms and vegetable tissues. The molecular structure of the approximately 120 GLs currently isolated and characterised consists of a common functional group and a lateral chain which can be of aliphatic, aromatic or heteroaromatic type.

The GLs, in the presence of the enzyme MYR (thioglucoside glucohydrolase, EC 3.2.3.1), are hydrolysed with formation of β-D-glucose, sulphate ion and a number of derivatives such as isothiocyanates, nitrites or thiocyanates (see, for example, Tookey H. L., Van Etten C. H., Daxembichler M. E., *Toxic Constituent of Plant Foodstuffs*, edited by I. E. Liner, 1980, II edition, 4, 103-142).

Some of the above-mentioned derivatives of the GLs, in particular the isothiocyanates, have shown in vitro cytotoxic properties towards nematodes (see Lazzeri L., Tacconi R., Palmieri S., In Vitro Activity of Some Glucosinolates and Their Reaction Products toward a Population of the Nematode *Heterodera schachtii*, *J. Agric. and Food Chem.* 1993, 41, 825-829) and plant fungal pathogens present in the soil (see, for example, Manici L. M., Leoni O., Lazzeri L., Galletti S., Palmieri S., Fungitoxic Activity of Some Glucosinolate Enzyme Derived Products Against the Main Soil-Borne Pathogens, *Pesticide Science*, 1999, 55, 486-488; and Manici L. M., Lazzeri L., Palmieri S., In Vitro Fungitoxic Activity of Some Glucosinolates and their Enzyme-derived Products toward Plant Pathogenic Fungi, *J. Agric. and Food Chem.* 1997, 45, 2768-2773).

To obtain and use the above-mentioned derivatives of the GLs, extraction and/or production procedures are necessary, which are relatively complex and costly and can also cause environmental problems (for example disposal of the by-products and/or the solvents used). Furthermore, generally some important derivatives of the GLs (for example allyl-isothiocyanate) are relatively difficult to handle as they have a relatively high volatility. To overcome these negative aspects the technique of green manure of plants containing both GLs and the enzyme MYR (i.e. containing the GLs-MYR system) has been proposed.

The green manure technique of plants containing the GLs-MYR system has some negative aspects, however, typical of the green manure technique in general. In particular, the green manure technique requires cultivation operations that determine relatively high labour costs and causes the loss of at least one growing cycle, with consequent damage for the farmer due to loss of income.

DISCLOSURE OF INVENTION

The aim of the present invention is to provide a use of a seed flour as a soil improver in order to reduce the above-mentioned disadvantages in a relatively simple and inexpensive way.

The present invention provides a use of a seed flour containing at least one glucosinolate and at least one enzyme chosen from the group consisting of:
glucosidasic enzymes, and
thioglucosidasic enzymes;
as a soil improver.

A further aim of the present invention is to provide a use of a seed flour as a cytotxic agent for soil pathogens and parasites.

The present invention provides a use of a seed flour containing at least one glucosinolate and at least one enzyme chosen from the group consisting of:
glucosidasic enzymes, and
thioglucosidasic enzymes;
as a cytotoxic agent for soil pathogens and soil parasites.

A further aim of the present invention is to provide a use of a seed flour as a fungitoxic agent.

The present invention provides a use of a seed flour containing at least one GL and at least one enzyme chosen from the group consisting of:
glucosidasic enzymes, and
thioglucosidasic enzymes;
as a fungitoxic agent for fungal pathogens of the soil.

Further characteristics of the present invention will be better clarified by the following non-restrictive description.

BEST MODE FOR CARRYING OUT THE INVENTION

Seeds containing GLs and at least one glucosidasic or thioglucosidasic enzyme are ground in order to obtain a fine uniform flour. Preferably the seeds contain the enzyme MYR, more preferably they belong to plants in the order of the Capparales and to the families of the Akaniaceae, Bataceae, and even more preferably they are seeds of *Brassicaceae, Capparaceae, Caricaceae, Gyrostemonaceae, Limnanthaceae, Moringaceae, Pentadiplantdraceae, Koeberliniaceae, Resedaceae, Salvodoraceae, Tropeolaceae* and/or *Toviaraceae*.

Preferably the seeds used are seeds of *Brassicaceae* and/or *Capparaceae*, in particular they are seeds of *Brassica carinata* A. B., seeds of *Eruca Sativa* M., and/or seeds of *Barbarea verna*. Furthermore, it is important to point out that it is possible to identify other vegetable varieties, the seeds of which contain GLs and a glucosidasic or thioglucosidasic enzyme, analysing the seeds by means of known methods.

The seed flour thus obtained has a variable content of GLs, glucosidasic or thioglucosidasic enzyme, proteinic material and oil according to the vegetable varieties and/or the ambient growing conditions. Furthermore, it is important to underline that when the vegetable varieties used vary, the related quantities of the different types of GLs contained in the seeds can also vary.

For each vegetable variety the best growing techniques can be identified (i.e. by optimising, for example, the sowing period, density, type of soil and/or fertilising agents) in order to obtain a higher content of GLs and glucosidasic or thioglucosidasic enzyme in the seeds.

It should also be noted that, preferably, to further increase the content of GLs and glucosidasic or thioglucosidasic enzyme, the above-mentioned seed flour is de-oiled, in other words it is treated in order to extract at least part of the oil contained in it. The extraction is performed preferably at a relatively low temperature, preferably below 75° C., in particular at ambient temperature, so that the glucosidasic or thioglucosidasic enzyme is not thermally deteriorated and, also after the oil extraction phase, it is still able to perform its enzymatic activity. In this regard it is important to underline that the oil extracted can be used, for example, as a renewable and ecologically sustainable lubricant or hydraulic fluid.

The flour, prepared in the form of pellets, can be distributed over the soil relatively easily and at a relatively low cost. In the presence of water, derivatives of the GLs generated by hydrolysis catalysed by the glucosidasic or thioglucosidasic enzyme develop in the soil. In this regard, it is important to underline that in order to hydrolyse the GLs, water is required, which is a reagent essential for triggering and developing the biochemical reaction.

For this reason, the non-hydrated flour has a relatively high stability, can be fairly easily transported, stored for relatively long periods and used at any time, regardless of the ambient conditions.

Once the flour has been distributed on the soil and hydrated, the derivatives of the GLs generated by enzymatic hydrolysis are able to perform their cytotoxic action even though the flour contains approximately 50% protein. Therefore, although it may be feared that the isocyanates generated by hydrolysis of the GLs, catalysed by the glucosidasic enzymes, or more specifically by the thioglucosidasic enzyme MYR, may spontaneously interact with the free NH2 groups of the lysines and arginines contained in the proteins, to produce adducts of a different type that can be referred to derivatives of thiourea, the hydrolysis products of the free GLs are surprisingly still able to perform a relatively high improving action in the soil. The hydrolysis products of the GLs perform a fungitoxic action, in particular on fungal pathogens of the soil belonging to different taxonomic classes (for example Oomycetes: *Pythium* and *Phytophthora*; Sterile fungi: *Sclerotium rolftsii* and *Rhizoctonia solani*; Hyphomycetes: *Fusarium* spp. and *Alternaria* spp.) and a cytotoxic action on soil pathogens and parasites, in particular nematodes (in particular *Meloidogyne incognita*), insects and weeds. Among the insects on which cytotoxic action is performed, the cytotoxic activity on wireworms is particularly interesting (for example *Agriotes sordidus, Agriotes utulatus* and *Agriotes brevis*). The fungitoxic activity on fungi in the genus *Fusarium* is also particularly interesting.

It is important to point out that use of the flour permits exploitation of concentrations of GLs substantially impossible to achieve with the green manure technique.

Note that it is possible to use either flour of seeds of one single vegetable variety, or a mixture of flour of seeds of a number of vegetable varieties. In particular, the varieties used for their seeds can be chosen so as to create flour formulates with different modes of action, according to the need for persistence or volatility of the derivatives of the GLs and the required cytotoxic action. In fact, both characteristics (volatility and cytotoxic action) can vary according to the type of pathogen or parasite and the phase it is in at the time: vegetation (like mycelium) or conservation (sclerotium, oospore, chlamydospore or hibernating mycelium). Therefore, according to the modes of application (times and types of culture) of the target pathogen(s) and/or parasite(s) and the need for improvement, the compositions of the formulates can be varied. In this way it is also possible to obtain formulates for the control of telluric pathogens and parasites. Furthermore, it is possible to use the flour described above also in combination with other compounds, which in their turn can be of either synthetic or natural origin.

Further characteristics of the present invention will become clear from the description of some merely illustrative and non-restrictive examples. In particular, although the following examples refer to the use of seed flour of *Brassica carinata* A.B, *Eruca sativa* M. and *Barbarea verna* as fungitoxic agents, the types of flour that can be used for said purpose are all those containing GLs and a glucosidasic or thioglucosidasic enzyme (in particular MYR). Furthermore, the flour containing GLs and a glucosidasic or thioglucosidasic enzyme (in particular MYR) can be used also as a cytotoxic agent for other soil pathogens and parasites.

It is important to point out that the results illustrated in the following examples can vary in quantitative but not qualitative terms, according to the vegetable varieties and ambient conditions in which the seeds are produced.

EXAMPLE 1

This example describes a method for obtaining seed flour of *Brassica carinata* A.B, *Eruca sativa* M. and *Barbarea verna*.

Seeds of *Brassica carinata* A.B, *Eruca sativa* M. and *Barbarea verna* are cleaned and then ground separately with an ordinary rolling machine until a fine uniform flour is obtained. Each type of flour is separately de-oiled with n-hexane (Carlo Erba®) in a concentration of 1:10 (weight/volume), leaving the suspension to be stirred in an agitator for 12 hours at ambient temperature. Each type of flour is then separately filtered on paper (Omniafiltra Supervelox filter, Cartiera del Torano SpA, Naples), washed repeatedly again with n-hexane and placed in a ventilated environment at ambient temperature for 24 hours in order to eliminate all remains of solvent.

EXAMPLE 2

This example describes an analysis method to determine the content of GLs and the mirosinasic activity in seed flour.

Each type of flour, obtained as described in example 1, was analysed to determine the content in GLs, using the procedure established by the regulation of the European Union 1864/90 for the analysis of rape seed (Official Journal of the European Communities, L 170, Mar. 7, 1990, p. 0027-0034). The analysis was performed with HPLC technique (High Performance Liquid Chromatography), using a Hewlett Packard® Chromatograph Mod. 1090L with diode detector ($\lambda$=229 nm) and a column HP ODS Hypersil C18, 5 µm 200×4.6 mm. The mobile phase consisted of a mixture of water and acetonitrile with a gradient from 1% to 22% of acetonitrile in 22 minutes and with a flow of 2 lm/min. The temperature of the column was 35° C.

Furthermore the total myrosinase activity in the flour was also quantified via the pH-stat assay (Palmieri S., Iori R., Leoni, O. Comparison of Methods for Determining Myrosinase Activity, J. Agric. Food Chem. 1987, 35, 617-621). The analyses were repeated three times, giving the results in Table I, after calculation of the means and standard deviations.

TABLE I

| Flour | GLs content (µmoli g$^{-1}$ TQ) | Prevalent GL | Myrosinase activity (U g$^{-1}$) |
|---|---|---|---|
| B. carinata | 141.6 ± 4.8 | Allyl GL (Sinigrine) | 34.7 ± 0.4 |
| E. sativa | 161.1 ± 2.1 | 4-Methylthiobutyl GL (Glucoerucin) | 53.3 ± 4.2 |
| B. verna | 143.7 ± 0.6 | Fenyl-ethyl GL (Nasturtin) | 2.4 ± 0.5 |

The data given in Table I indicate that after cold grinding and extraction with n-hexane, the GLs and the enzyme MYR in active form are present in the flour. Therefore the de-oiled seed flour of P *Brassica carinata* A.B, *Eruca sativa* M. and *Barbarea verna* contain the GLs-MYR system, and hence, in the presence of water, are able to produce derivatives of GLs generated by enzymatic hydrolysis via MIR.

The analysis method described above can be used to identify the vegetable varieties in the seeds of which the GLs-MYR system is present.

EXAMPLE 3

This example describes a method for assessing the fungitoxic activity.

The fungitoxic activity test was performed starting from an isolate of *Fusarium culmorum*, isolated and identified as in Manici M. L. and Cerato C. (1992)—Studio su alcuni funghi agenti di marciume dei tuberi di patata; Informatore Fitopatologico 9: 41-46, and references quoted in it. This isolate is catalogued as fungo test at the micotech of the Experimental Institute for Industrial Cultivation (Bologna) and was chosen for the stability and regularity of growth that characterise it.

The test provided for assessment of the toxicity of the volatile compounds released by the flour following hydration.

Doses of 0.01 g, 0.025 g, 0.05 g, 0.25 g and 1 g of the seed flour of *Brassica carinata*, *Eruca sativa* and *Barbarea verna* analysed in example 2 were tested separately. The control, included for assessment of the fungitoxic activity, consisted of pellets of commercial organic soil improver based on fowl dung and torrefied leather.

The assay was based on assessment of the reduction of growth in colonies of *Fusarium culmorum* in the presence of the products released by the flour following hydration, with respect to growth of the same fungus in the presence of the control.

Colony discs of 4 mm taken from a one-week old colony of *Fusarium culmorum* were inoculated on a bottom of a Petri dish on an agar nutritive substrate (Potato Dextrose Agar) and immediately after overturned onto a bottom of a Petri dish containing the control and, separately, the flour in the different amounts (in a total volume of approximately 174 cm$^3$) hydrated immediately beforehand. The two Petri dish bottoms joined as above were sealed with parafilm, and the resulting dishes incubated for the time necessary for the colony on the control to develop and invade at least ¾ of the dish. At this point the diameters of the colonies grown in the presence of the vapours released at the different doses of flour and control were measured.

The fungitoxic activity of the flour was expressed as inhibition effectiveness (EI) as a percentage with respect to the control, using the formula:

$$EI(\%)=[(\text{Diameter of Control}-\text{Diameter of Treated Sample})/\text{Diameter of Control}]\times 100.$$

Table II shows the results of the test.

The test was performed with three repetitions per treatment, therefore the data shown in table II are the means of three values.

TABLE II

| Treatment De-oiled flour | Dose (g/dish) | EI % |
|---|---|---|
| *Eruca sativa* | 0.01 | 81 |
|  | 0.025 | 100 |
|  | 0.05 | 100 |
|  | 0.25 | 100 |
|  | 1 | 100 |
| *Brassica carinata* | 0.01 | 72 |
|  | 0.025 | 100 |
|  | 0.05 | 100 |
|  | 0.25 | 100 |
|  | 1 | 100 |
| *Barbarea verna* | 0.01 | 40 |
|  | 0.05 | 100 |
|  | 0.25 | 100 |
|  | 1 | 100 |

The above data indicate that the products released by the seed flour of *Brassica carinata* A.B., *Eruca sativa* M. and *Barbarea verna*, following hydration, which activates the GLs-MYR system present in it, inhibit to a large extent growth of the fungus *Fusarium culmorum*.

EXAMPLE 4

This example describes a method for assessing the nematocide activity on nematodes, in particular root knot nematodes.

The nematocide activity test was performed with larvae of *Meloidogyne incognita* (Kofoid and White) Chitwoody, from soil in the Ferrara area.

The test was performed in jars with capacity of 100 g of soil to which second age larvae had been added in order to assess the toxicity of the volatile compounds released by the flour following hydration.

The doses equivalent to $20.10^{-2}$, $40.10^{-2}$ and $120.10^{-2}$ Kg/m$^2$ of seed flour of *Brassica carinata*, *Barbarea verna* and *Eruca sativa* of example 2 were tested separately. The control, included for assessment of the nematocide activity, consisted of non-treated soil and a fertiliser with two different organic compounds: fowl dung and torrefied leather (applied at the maximum test dose, i.e. $120.10^{-2}$ Kg/M$^2$).

The test was based on assessment of the mortality of the larvae of *Meloidogyne incognita* in the presence of the flour and the non-biocide flour, with respect to the mortality in untreated soil.

The table shows the results of the test. The nematocide activity of the flour was expressed as the number of larvae remaining in the soil 10 days after the treatment.

The test was performed with four repetitions per treatment, therefore the data shown in table III are the means of four values.

TABLE III

| Treatment | Dose Kg/m2 | N° larvae 100 g of soil |
|---|---|---|
| Blank | — | 14 |
| Fowl dung | $40.10^{-2}$ | 8 |
| Leather | $40.10^{-2}$ | 5 |
| B. Carinata | $20.10^{-2}$ | 1 |

TABLE III-continued

| Treatment | Dose Kg/m2 | N° larvae 100 g of soil |
|---|---|---|
| B. Carinata | $40.10^{-2}$ | 0 |
| Eruca sativa | $20.10^{-2}$ | 0 |
| Eruca sativa | $40.10^{-2}$ | 0 |
| B. Verna | $20.10^{-2}$ | 2 |
| B. Verna | $40.10^{-2}$ | 2 |

The above data indicate that the products released by the seed flour of *Brassica carinata* A.B., *Eruca sativa* M. and *B. Verna* following hydration, which activates the GLS-MYR system present in it, inhibit to a large extent the presence of Meloidogyne larvae in the soil.

EXAMPLE 5

This example describes a method for assessing insecticide activity, in particular with regard to wireworms.

The insecticide activity test was performed with larvae of *Agriotes sordidus* Illiger, *Agriotes ustulatus* Schäller, *Agriotes litigiosus* Rossi and *Agriotes brevis* Candeze, produced on breeding farms in Veneto.

The test was performed in jars with capacity of 1.4 l of soil to which larvae of wireworms of the above species at the $6^{th}$-$8^{th}$ stage of development had been added in order to assess the toxicity of the volatile compounds released by the flour following hydration.

The doses equivalent to 20 and 40 quintals $ha^{-1}$ of seed flour of *Brassica carinata* and *Eruca sativa* of example 2 were tested separately. The control, included for assessment of the insecticide activity, consisted of untreated soil.

The test was based on assessment of the mortality of the larvae of Agriotes in the presence of the flour which had undergone hydration, with respect to the mortality in untreated soil. Assessment of mortality was performed one hour after addition of the flour to the soil.

Table II shows the results of the test. The insecticide activity of the flour was expressed as inhibition effectiveness (EI) as a percentage with respect to the control, using the formula:

$EI(\%)=[(\text{Mortality of Control}-\text{Mortality of Treated Sample})/\text{Mortality of Control}]\times 100$.

The test was performed with four repetitions per treatment, therefore the data shown in table IV are the means of four values.

TABLE IV

| Treatment with de-oiled flour | EI % |
|---|---|
| Eruca sativa | 92 |
| Brassica carinata | 100 |

The above data indicate that the products released by the seed flour of *Brassica carinata* A. B. and *Eruca sativa* M. following hydration, which activates the GLs-MIR system present in it, inhibit to a large extent the presence of Agriotes larvae in the soil.

In particular, the following were observed:
a high insecticide action of the above-mentioned seed flour in the space of only a few minutes;
a rapid disappearance of the active compounds (no insecticide activity in the space of only a few days);
consequent low environmental impact.

No negative interactions were observed.

The invention claimed is:

1. A method of killing soil pathogens and soil parasites comprising
   a contact step, during which at least one of a soil pathogen and a soil parasite is contacted with a composition comprising a seed flour containing at least one glucosinolate and the enzyme myrosinase, wherein the seed flour contains a seed selected from the group consisting of seeds of *Brassica carinata* A. B., seeds of *Capparaceae*, and seeds of *Barbarea verna*; wherein the seed flour has been de-oiled at a temperature below 75° C.; and
   a release step, during which hydrolysis of the glucosinolate takes place in the presence of water so that isothiocyanates are released from the composition to at least one of the soil pathogen and soil parasite.

2. The method of claim 1, wherein the soil parasites are selected from the group consisting of nematodes and wireworms.

3. The method of claim 1, wherein the soil parasites are selected from the group consisting of weeds and insects.

4. The method of claim 1, wherein the parasites are selected from the group consisting of *Fusarium clumorum*, *Meloidogyne incognita* (Kofoid and White) *Chitwoody*, *Agriotes sordidus*, *Agriotes utulatus*, and *Agriotes brevis*.

5. The method of claim 1, wherein the flour is fungitoxic to a fungi of the genus *Fusarium*.

6. A method of improving soil comprising a contact step, during which a soil is contacted with a seed flour containing at least one glucosinolate and the enzyme myrosinase, wherein the seed flour is toxic to at least one organism selected from the group consisting of a nematode, a wireworm, a weed, an insect, *Meloidogyne incognita* (Kofoid and White) *Chitwoody*, *Agriotes sordidus*, *Agriotes utulatus*, and *Agriotes brevis*, and a fungi of the genus *Fusarium*; wherein the seed flour has been de-oiled; and
   a release step, during which hydrolysis of the glucosinolate takes place in the presence of water so that isothiocyanates are released from the composition to the organism.

7. The method of claim 6, wherein the seed flour has been de-oiled at a temperature below 75° C.

8. The method of claim 6, and further comprising an identification phase to identify the seed flour containing at least one glucosinolate and at least one enzyme selected from the group consisting of glucosidasic enzymes and thioglucosidasic enzymes.

9. The method of claim 8, wherein the at least one enzyme is myrosinase.

10. A method of improving soil comprising
    a contact step, during which the soil is contacted with a flour made from at least one seed selected from the group consisting of seeds of *Brassica carinata* A. B., seeds of *Capparaceae*, and seeds of *Barbarea verna* wherein the flour has been de-oiled at a temperature below 75° C.; and
    a release step, during which isothiocyanates are released from the composition into the soil.

11. The method of claim 10, wherein the flour is toxic to at least one organism selected from the group consisting of a nematode, a wireworm, a weed, an insect, *Meloidogyne incognita* (Kofoid and White) *Chitwoody*, *Agriotes sordidus*, *Agriotes utulatus*, and *Agriotes brevis*, and a fungi of the genus *Fusarium*.

12. A method of improving soil comprising
    a contact step, during which the soil is contacted with a composition comprising a seed flour containing at least one glucosinolate and enzyme myrosinase, wherein the seed flour contains a seed selected from the group consisting of seeds of *Brassica carinata* A.B., seeds of *Capparaceae*, and seeds of *Barbarea verna*; wherein the seed flour has been de-oiled; and a release step, during which hydrolysis of the glucosinolate takes place in the presence of water so that isothiocyanates are released from the composition into the soil.

13. The method of claim 12, wherein the seed flour has been de-oiled at a temperature below 75° C.

14. The method of claim 13, wherein the seed flour has been de-oiled at ambient temperature.

15. The method of claim 12, wherein the seeds comprise seeds of *Brassica carinata* A.B.

16. The method of claim 12, wherein the seeds comprise seeds of *Capparaceae*.

17. The method of claim 12, wherein the seeds are of at least two different vegetable varieties.

18. The method of claim 1, wherein the seeds comprise seeds of *Brassica carinata* A.B.

* * * * *